(12) United States Patent
Skatter et al.

(10) Patent No.: US 6,757,354 B2
(45) Date of Patent: Jun. 29, 2004

(54) MULTI-VIEW X-RAY IMAGING OF LOGS

(75) Inventors: Sondre Skatter, Oakland, CA (US); Francois Mesqui, Palo Alto, CA (US)

(73) Assignee: InVision Technologies, Inc., Newark, CA (US)

( * ) Notice: Subject to any disclaimer, the term of this patent is extended or adjusted under 35 U.S.C. 154(b) by 30 days.

(21) Appl. No.: 10/251,203

(22) Filed: Sep. 20, 2002

(65) Prior Publication Data

US 2004/0057551 A1 Mar. 25, 2004

(51) Int. Cl.[7] .............................................. G01N 23/02
(52) U.S. Cl. ............................... 378/58; 378/4; 378/10; 378/62; 378/901
(58) Field of Search ........................... 378/4, 8, 10, 15, 378/19, 58, 62, 901

(56) References Cited

U.S. PATENT DOCUMENTS

| | | | |
|---|---|---|---|
| 4,135,247 A | 1/1979 | Gordon et al. | 364/414 |
| 4,916,629 A | 4/1990 | Bogue et al. | |
| 5,023,805 A | 6/1991 | Aune et al. | 364/507 |
| 5,257,101 A | 10/1993 | Lee | 358/101 |
| 5,394,342 A | 2/1995 | Poon | 364/558 |
| 5,960,104 A | 9/1999 | Conners et al. | 382/141 |
| 6,151,379 A | 11/2000 | Kullenberg et al. | 378/54 |
| 6,157,698 A | 12/2000 | Pietikainen et al. | 378/58 |
| 6,217,214 B1 | 4/2001 | Cabral et al. | 378/196 |
| 6,229,872 B1 | 5/2001 | Amos | |

OTHER PUBLICATIONS

Schmoldt, Daniel L. "CT Imaging, Data Reduction, And Visualization Of Hardwood Logs", Hardwood Symposium Proceedings, May 8–11, 1996, pp. 69–80.
Schmoldt, Daniel L.; Occena, Luis G.; Abbott, A. Lynn; and Gupta, Nand K. "Nondestructive Evaluation Of Hardwood Logs: CT Scanning, Machine Vision And Data Utilization" Nondestr. Test. Eval., vol. 15, pp. 279–309.
Skatter, S., "Determination of Cross–Sectional Shape Of Softwood Logs From Three X–Ray Projections Using An Elliptical Model" Holz als Roh– und Werkstoff 56 (1998) 179–186. © Spring–Verlag 1998.

*Primary Examiner*—David V Bruce
(74) *Attorney, Agent, or Firm*—Bever, Hoffman & Harms, LLP; James E. Parsons (57) ABSTRACT

A method and apparatus is disclosed for mapping the relevant material properties of a log, such as knot location and extent. The outer shape of the log under bark is also revealed using this method, and the boundary between the heartwood and sapwood is accurately mapped. The apparatus includes three x-ray sources and arrays of x-ray detectors, for measuring the attenuation of the wood in the log. Deviations in attenuation are related to changes in density, which are indicative of knots and other defects. Accurate estimates of shape, density and knot location render improved sawing decisions at the headrig of a sawmill, which improve the yield of high quality lumber from a given log. The techniques may also be used in a system for sorting logs according to quality.

55 Claims, 7 Drawing Sheets

MULTI-VIEW X-RAY IMAGING OF LOGS

CROSS-REFERENCE TO SOFTWARE APPENDIX

Per the requirements of 37 C.F.R. §1.96, a Computer Program Listing Appendix is a part of this disclosure and is incorporated by reference. The Computer Program Listing, Appendix A, is contained on a total of two CD-ROM's, consisting of a first copy, "Copy 1," and a duplicate copy, "Copy 2." Appendix B, which is also part of the present specification, contains a list of the files contained on the compact disk(s), and is attached herewith. The files of Appendix A form source code of computer programs and related data of an illustrative embodiment of the present invention. The CD-ROM is in IBM-PC format and compatible with MS-Windows.

A portion of the disclosure of this patent document contains material, which is subject to copyright protection. The copyright owner has no objection to the facsimile reproduction by anyone of the patent document or the patent disclosure, as it appears in the U.S. Patent and Trademark Office patent files or records, but otherwise reserves all copyright rights whatsoever.

BACKGROUND

1. Field of the Invention

This invention relates to x-ray imaging of internal structures of solid bodies, and the particular examples relate to the determination of the location and geometry of defects internal to logs.

2. Discussion of Related Art

The variability of logs in terms of shape and quality is a major challenge for modern sawmills. To optimize the output of each individual saw log, information as to the shape and quality has to be known prior to sawing. Two different strategies are used to optimize the log breakdown. In European softwood mills the logs are pre-sorted according to dimensions and sometimes quality. Usually, optical scanners provide the data on which the sorting is based. Then, each sorted group of logs is sawed with the identical sawing pattern. In most cases the sorting is done while the bark is still on. A limitation of optical scanners is that they only measure the external shape of the log, whereas the more relevant shape under bark remains unknown. The dimensions under bark are often estimated using a statistical bark thickness function. Variations in bark thickness thus cause sorting errors. The other strategy is to optimize the sawing pattern of each individual log. This is common in mills processing higher-value logs such as hardwood or large-diameter softwood logs. In both cases, information about the external shape as well as the internal quality—the locations and distributions of defects—is needed to make the best decision.

Internal log scanners are a class of scanners, which provide information about the interior of the logs. X-ray imaging has for several years demonstrated the ability to reveal the location and geometry of internal structures in logs, which will serve as a means for improving the yield of quality lumber after sawing of the logs. Knowledge of the internal structures, such as knots, will improve the sawing decision by rotating the log into a known orientation upon presentation to the primary breakdown in the sawmill. In some cases like in pruned planted pines (Radiata Pine, Southern Yellow Pine), the knot core of the log will be measured, and thus the yield of high-quality lumber free of knots from a given log is improved.

It remains a challenge to the timber industry to develop and implement algorithms for most effectively analyzing the data generated by x-ray sources and detectors. One approach is set forth in Aune et al. in U.S. Pat. No. 5,023,805, where a three-view x-ray apparatus is disclosed. This system detects the knots in the x-ray views and applies a convex hull method to determine the knot geometry. The application of the system is optimization of the primary breakdown on a band saw. In Pietikainen et al., U.S. Pat. No. 6,157,698, an evidence value representative of the presence of a knot in a particular volumetric element of a log is calculated, and the evidence values of mutually associated elements are combined to produce an aggregate evidence value. The evidence value is used to sort logs according to their apparent quality.

The methods disclosed in the prior art suffer from a number of disadvantages. For instance, the methods cannot distinguish the outline of the bark from the shape of the log under the bark, since a simple laser profile scanner is used to detect the shadow edges of the log. Therefore, the true shape of the log under bark cannot contribute to the selection of a sawing decision or to a measurement of the density of the wood. Also, the convex hull method described in U.S. Pat. No. 5,023,805 does not effectively address the situation in which several defects are located in the same log cross section. Therefore, the ability of the prior art approaches to identify and locate defect information corresponding to knots in the wood is limited. Hence, an improved approach is desirable.

SUMMARY OF THE INVENTION

The present invention offers significant improvement in terms of modeling the shape of the heartwood/sapwood boundary and the bark thickness. This modeling is useful in terms of describing the geometry of the log, but has a further advantage in that it allows for more precise mapping of internal defects in the log, such as knots. A further improvement lies in the incorporation of knowledge of the morphology of the tree anatomy into the mapping method, to discriminate between knots and clear wood.

Embodiments of the invention make use of two or more x-ray sources, which emit radiation, which impinges upon a solid body whose internal structures are to be characterized. Each of the x-ray sources has a corresponding sensor, which is an array of individual detectors arranged side-by-side and on the opposite side of the body from the source, and in a circumferential pattern so that the individual detectors form an arc whose center is at the location of the source. In the example, the solid body is a wood log, and the internal structures of interest include the heartwood, sapwood, knots and other defects, as well as inclusions such as metal spikes or nails. The radiation is transmitted through the body as a function of its density, such that higher density structures, such as knots, attenuate the radiation more substantially than lower density areas, such as heartwood.

By measuring differences in the transmitted intensity between adjacent detectors, the ray paths which just intersect a boundary between two regions of different density can be determined, and a tangent line is calculated which just intersects a boundary between the regions. The differences in the higher order features of the transmitted intensity, such as texture and gradient, may also contain information as to boundaries between defects and clear wood, or between different categories of clear wood. Knowing the location of the source allows an equation for the tangent line to be calculated, and an estimate of an ellipsoidal shape is determined, which would approximate the detected signal. The method assumes an arbitrarily oriented ellipse as the model shape, and the tangent lines are fitted to the model. An improved model shape is obtained by using an interpolation correction between the measured attenuation values and the model predictions.

By transporting the log past the sources and sensors in a direction perpendicular to the paths of the x-ray radiation, a longitudinal projection view of the log is generated, with each detector imaging a single chord through the body of the log. Low frequency (slowly varying) changes in this detected signal are indicative of variations in the width of the log, or its curvature. Higher frequency variations are indicative of knots or other defects within the wood of the log. The knot signal is separated from the wood signal, for example, by applying a high pass filter to the signals corresponding to a longitudinal axis of the log. The filter produces a map in which high frequency changes in density are highlighted, and correspond to the longitudinal locations of knots. The trajectories of the knots are computed by performing a line parameter space (Hough) transform of the candidate knot areas. The Hough transform method gives a more confident determination of the knot trajectory, compared to methods disclosed in the prior art.

Among the relevant pieces of information revealed by these techniques are the shape under bark, heartwood/sapwood boundary, density, location and extent of knot core, location and number of annual rings, and the presence and quantity of needle flecks. This information can then be used either to grade or sort logs according to knot properties, or it is used to optimize the sawing decision at the primary breakdown of the mill.

These and other features of the present invention will be readily understood with reference to the following detailed description of the exemplary embodiments taken in conjunction with the accompanying drawings thereof.

BRIEF DESCRIPTION OF THE DRAWINGS

In the foregoing figures, like reference numerals designate like structural elements.

DETAILED DESCRIPTION OF THE INVENTION

Figure 1:
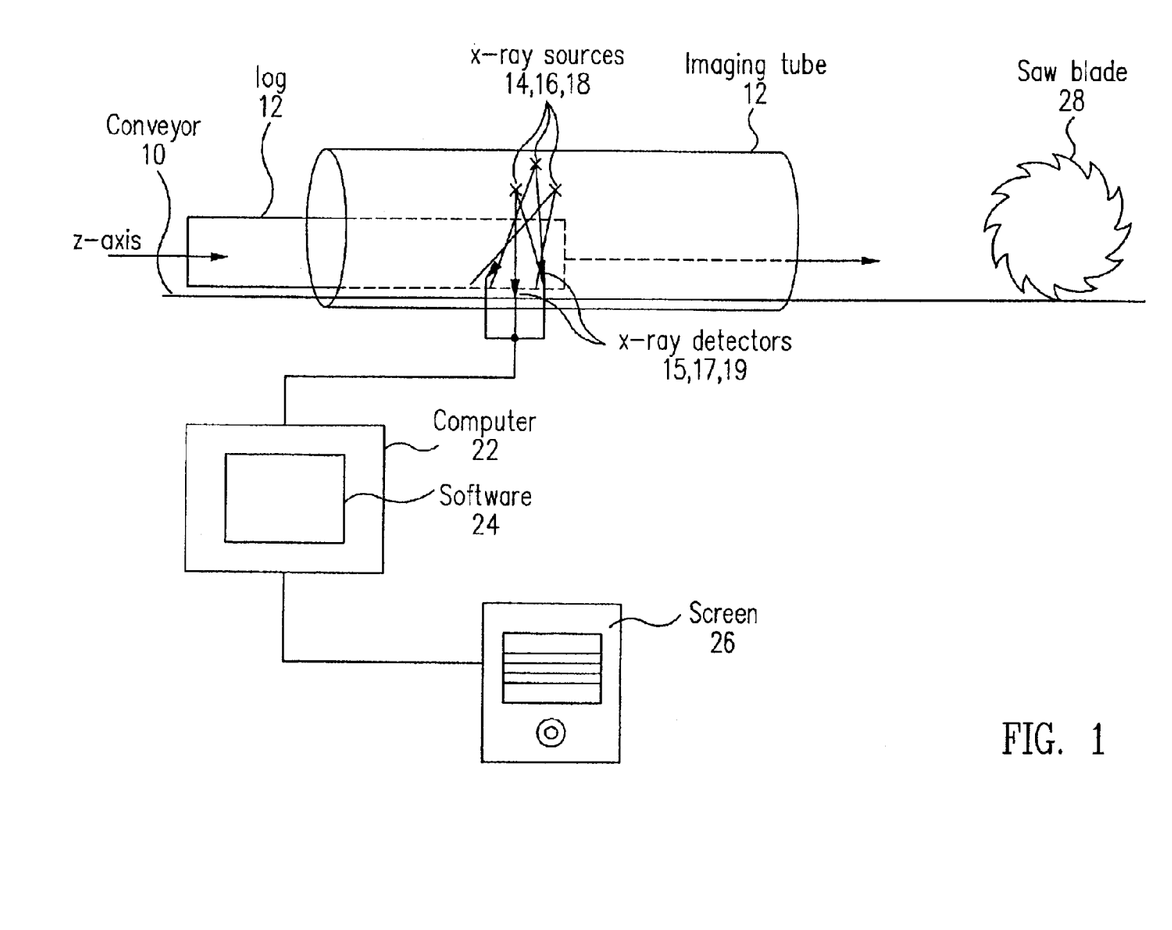
FIG. 1 is a schematic diagram of a system configuration of an x-ray log imaging apparatus.

An exemplary embodiment of the invention applies three x-ray sources disposed adjacent to the conveyor path of solid objects, such as logs (e.g. Radiata Pine), being transported through a processing plant. A diagrammatic view of the apparatus is shown in FIG. 1. This embodiment uses x-ray sources, although it is clear that other wavelengths of electromagnetic radiation could also be used. The conveyor 10 transports the logs 12 in a direction parallel to the central longitudinal axis of the log, designated the z-axis in the figure. Three x-ray sources 14, 16, and 18 may be disposed around the body of the log, where they emit electromagnetic radiation perpendicular to the path of travel of the log, and the radiation is detected by sensors 15, 17, and 19 arranged on the opposite side of the log. The sensors feed their output to a computer 22, on which software 24 for use with the methods disclosed herein, is installed. The computer 22 displays the data on a screen 26 to an operator, or the method may be implemented in a fully automated system. The conveyor transports the log past the sources 14, 16, and 18 and detectors 15, 17, and 19, to the next step of the mill process, which can be either sorting or primary breakdown.

Figure 2:
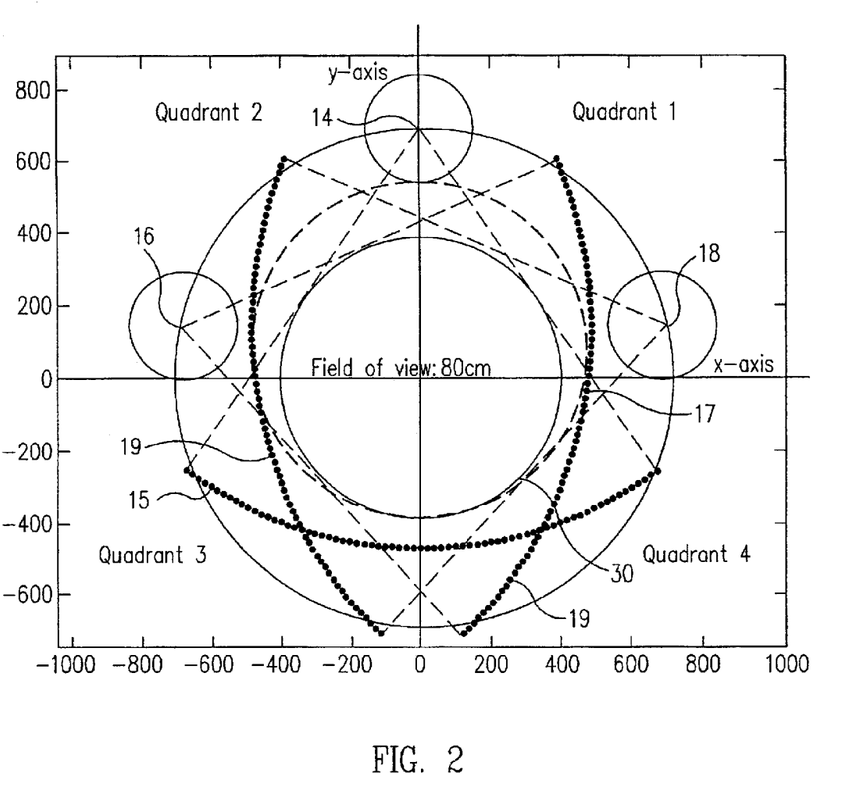
FIG. 2 is a schematic diagram of the x-ray log imaging geometry, superimposed upon an x-y coordinate plane.

The x-ray sources are disposed circumferentially around the log, as shown diagrammatically in FIG. 2. A feature of the present invention is that, for a three-source system, the angle between these sources is not 120 degrees, as is conventional, but rather is less than 120 degrees. For instance in the embodiment shown in FIG. 2, where the centerline of the log is at the origin of the x-y coordinate system, a first x-ray sensor 14 is on the y-axis (90 degrees), and a second and third sensors 18 and 16 are disposed in quadrants 1 and 2, equidistant from the first sensor 14. The angle between sensor 14 and each of sensors 16 and 18 is less than 90 degrees, e.g. in a range of 70 to 80 degrees, or in this particular example, at an angle of approximately 76 degrees. The optimum separation angle $\theta_{opt}$ for a given operation will depend in general on the locations of the sources and detectors, the fan angle of the source, and the distribution of log sizes. The optimum angle is quite sensitive to the size distribution, and the value of 76 degrees pertains to the size distributions typical of a Radiata Pine operation.

The optimum separation angle $\theta_{opt}$ is obtained by an analysis method, which estimates the most effective location for the three sources and three sensors, given that each source has a fan angle of 70 degrees, which generates a limited field of view.

The field of view as depicted in FIG. 2 is the polygon, or inscribed circle, 30, which is intersected by all the x-ray views in the system. The fan beam angle, together with the distance to the imaging center, determines the field of view. Due to the fan beam geometry, the independence of the views varies within the field of view. If one defines independence of views as the angular distribution of the tangents to the log outer shape boundary, and the heartwood core boundary, one can compare the distribution of angles for various source separations. The tangent lines are the ray paths, which just intercept the outside boundary, or the heartwood core, of the sample log. It is advantageous to sample the boundaries at points as widely separated as possible, in order to form the best approximation for the shape of the log.

In this example, the analysis was performed for various log diameters, using a field of view of 95 cm, and a fan angle of 70 degrees, so that the distance to the center of the log was 83 cm. The distribution of angles for tangent points about a circular sample were compared, based on the placement of the sources. The results of the analysis showed that the 120-degree separation was not optimal, because at least two of the tangent lines essentially overlapped. Therefore the data they yielded was not independent. The analysis showed that a source separation, $\theta_{opt}$, of about 76 degrees is optimal because the tangent points are maximally distributed compared to having the sources equidistant. Therefore, the optimum separation angle $\theta_{opt}$ yields more independent data, because the six tangent lines are well distributed around the circumference, whereas in the 120 degree separation, pairs of tangent lines are similar in orientation.

The separation $\theta_{opt}$ is optimal for both the separation of tangent points around the outer boundary, as well as around the inner boundary of the heartwood core. The positioning of the sources 14, 16 and 18 relative to the imaged log 30 and the sensors 15, 17 and 19, is shown schematically in FIG. 2. Sensor 14 is on the y-axis, and sensors 16 and 18 are in quadrants 2 and 1, respectively.

Because the angular separation $\theta_{opt}$ between the sources may be less than 120 degrees, the sources and the sensors may be placed in separate planes along the z-axis, to keep the sensors from physically interfering with one another, as they would if they were all located in the same cross sectional plane. Therefore, in this example, the sources and sensors are located in different planes, and separated from one another by 3–5 cm, along the longitudinal axis of the log.

Individual detectors which make up the sensors 15, 17, and 19, are arranged side-by-side, each separated by about 2 mm, in a circumferential arrangement whose nominal center is at the x-ray source, as was shown in FIG. 2. The arc angle covered by the detectors matches the fan angle of the x-ray bean, e.g. 70 degrees. The field of view of each of the detectors is clipped by a set of lead shutters, which permit only collimated x-rays to enter the detector, and absorb any off-axis rays. The detectors may be cadmium tungsten scintillators, which fluoresce in the visible spectrum when excited by an x-ray photon. The visible fluorescence is detected by a photodiode, which produces a current or voltage proportional to the amount of light incident upon it. The output of the photodiode is digitized to produce a digital output, which is proportional to the amount of x-ray flux transmitted through the solid body. The signal is plotted as an attenuation signal, where a higher signal level corresponds to a greater attenuation, which corresponds in turn to a higher density material intervening between the detector and the source.

The detectors are calibrated before use by measuring the amount of signal without the log present. This is the gain of the detector. The detector offset is measured by measuring the detector output with the x-ray source turned off. The measured signal level is based on these two correction factors, and is given by $$-\ln[(\text{signal-offset})/(\text{gain-offset})] = \mu \rho L$$

where $\mu$ is the mass attenuation coefficient of the wood, $\rho$ is the average density along the path length through the wood, and L is the path length through the wood. The measured signal must also be corrected for the beam hardening effect, which involves the tendency of the softer x-rays to be absorbed preferentially to the hard x-rays, which causes a shift in the spectral content of the x-ray beam towards harder x-rays. A correction for this can be obtained by simply consulting a lookup table, implemented in software 24 of FIG. 1., which converts a measured attenuation to a corrected value for the mass attenuation coefficient of the intervening material and the given x-ray spectrum.

The detector arrays are composed of a side-by-side arrangement of detectors in an arc segment around the log, as indicated in FIG. 2. Each adjacent detector samples a different transverse path in the log. Therefore, the output of the detectors in the array is related to the path length and density of the different paths through the log. For example, for rays tangent to the body of the log, an abrupt change in the transmitted signal is detected when monitoring the output signal of detectors which lie across the shadow boundary of the log. In the shadow of the log, an attenuated signal is measured which is the product of the mass attenuation coefficient $\mu$ of the x-rays traveling in the wood, times the average density of the material $\rho$, times the path length L, of the ray traveling through the wood. Outside of the shadow area, in a clear path, the x-rays reach the detector essentially unobstructed.

Figure 3:
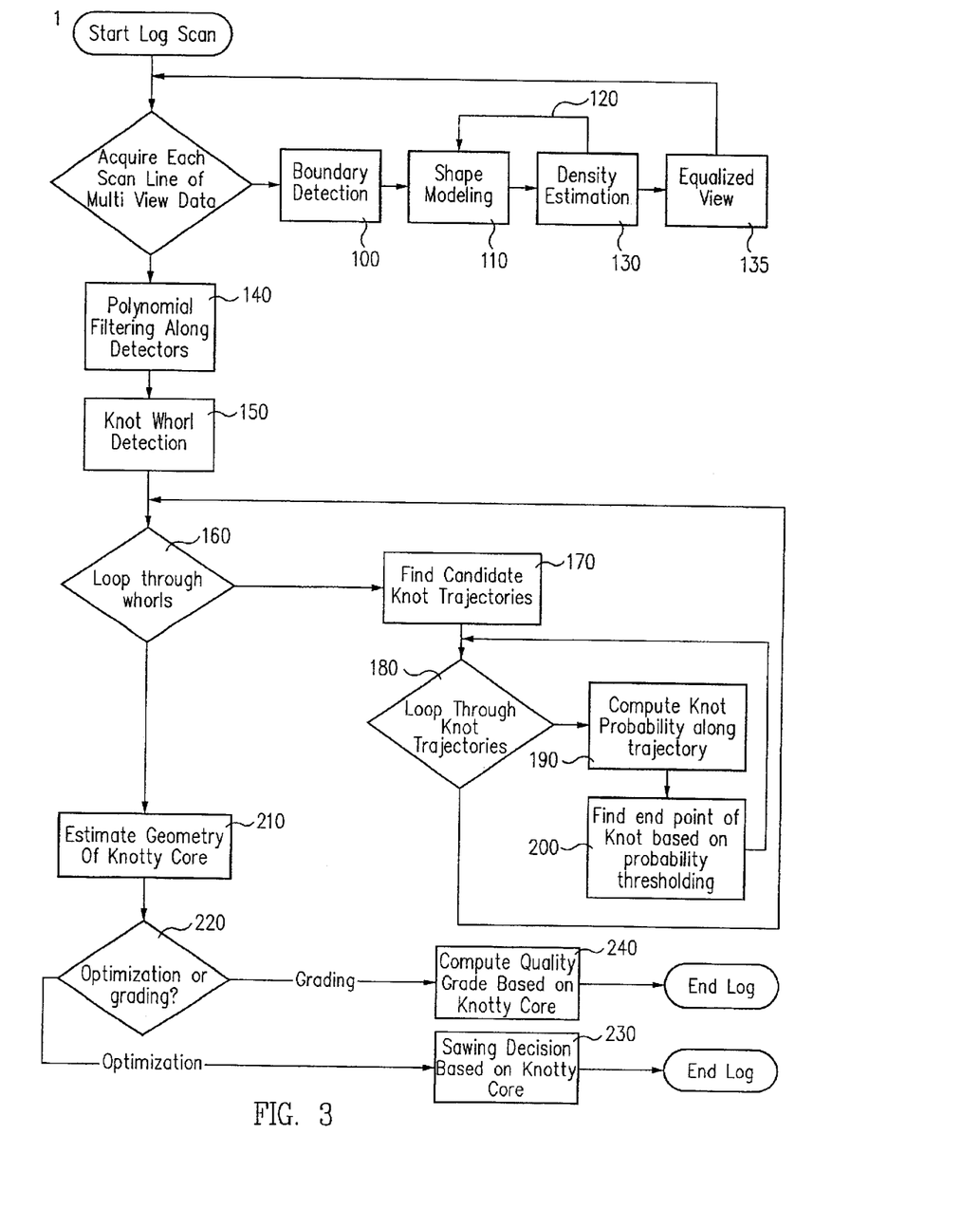
FIG. 3 is a flow chart outlining the method of this invention.
Figure 4:
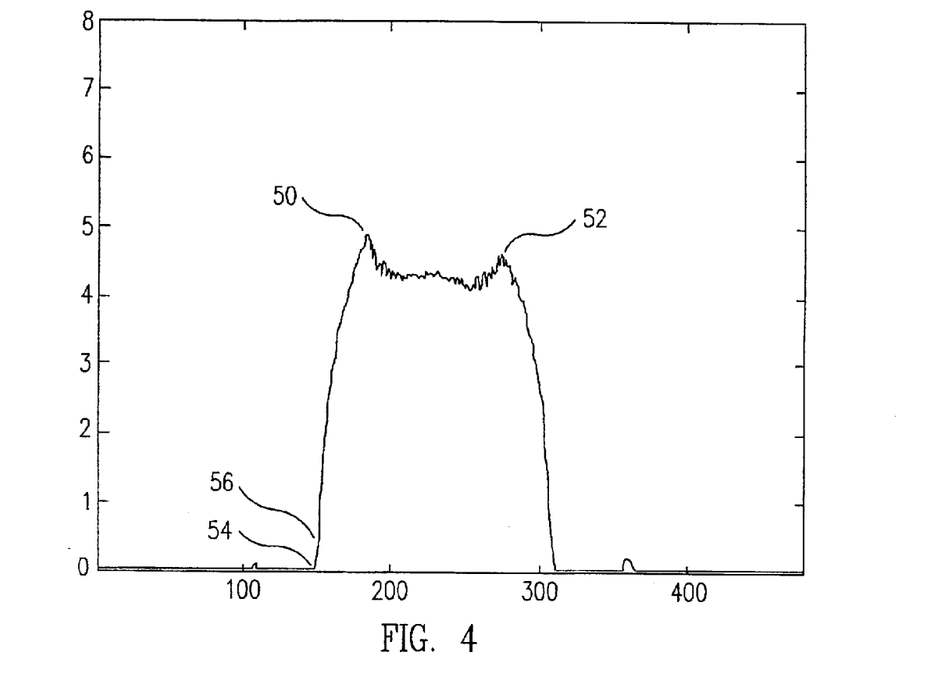
FIG. 4 is a typical signal taken across the detector array, indicating the boundaries of internal structures in the log.
Figure 5:
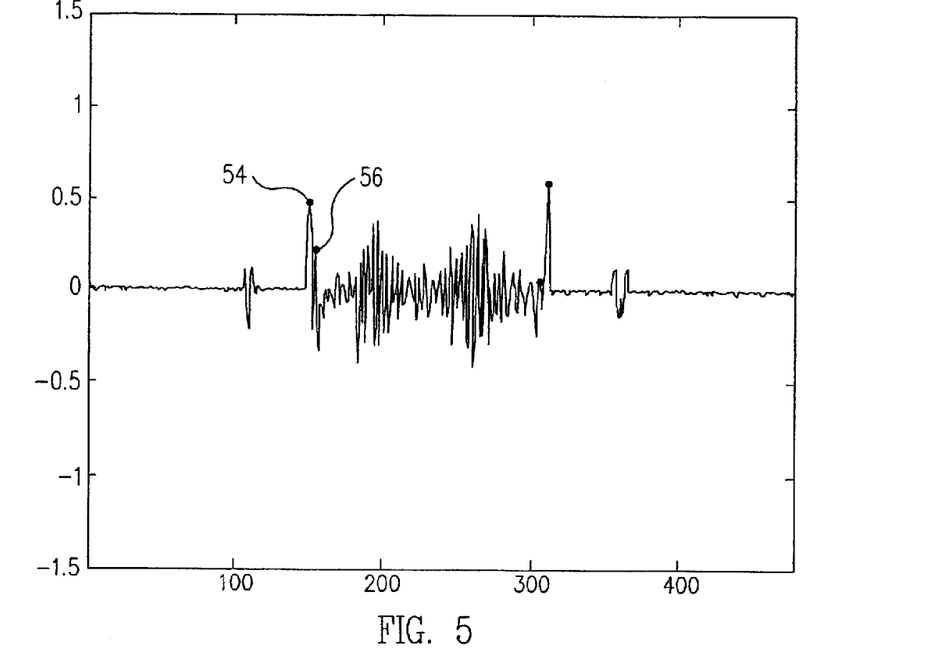
FIG. 5 is a graph of the second derivative of the signal shown in FIG. 2.

The flow chart depicted in FIG. 3 gives a process flow for an exemplary implementation of the invention. A computer 22 (FIG. 1) measures and stores the output level of each of the detectors in the array. FIG. 4 is a graph of a typical set of data taken across the detector array, demonstrating the boundary between a clear path and a shadow path. The first detector lying within the shadow path samples radiation that passes mainly through the outer bark of the log and not through the interior wood. Therefore, a first boundary, labeled 54 in the figure, can be detected which occurs at the boundary between the clear path and the bark edge, and is followed by a second boundary, labeled 56, which occurs between the outer bark and the sapwood of the log. This boundary is relatively subtle, but becomes apparent in the second derivative of the signal, which is calculated by twice applying the convolution [−1 0 1] across the detector array values. The second derivative, plotted in FIG. 5, of the data set shown in FIG. 4, highlights changes in the slope of the attenuated signal, which occur at the boundary between two regions with different density. The maximum value of the second derivative signal corresponds to the first interface between the bark and the clear path, and is indicated as point 54 in the figure. The next maximum after this first boundary, relates to the bark/sapwood boundary, and is indicated as point 56 in the figure. Detection of the width of the bark allows a more accurate estimation of the true outer shape of the log, compared to profile scanners used in the prior art.

The second boundary, 56, between the bark and the sapwood, marks the true outer useable limit of the log. This location in the detector array, as determined by the occurrence of the second peak in the second derivative signal, is measured relative to the location of the x-ray source, and defines the tangent to the body of the log. Knowledge of this tangent line allows an estimation of the true outer shape of the log.

Figure 6:
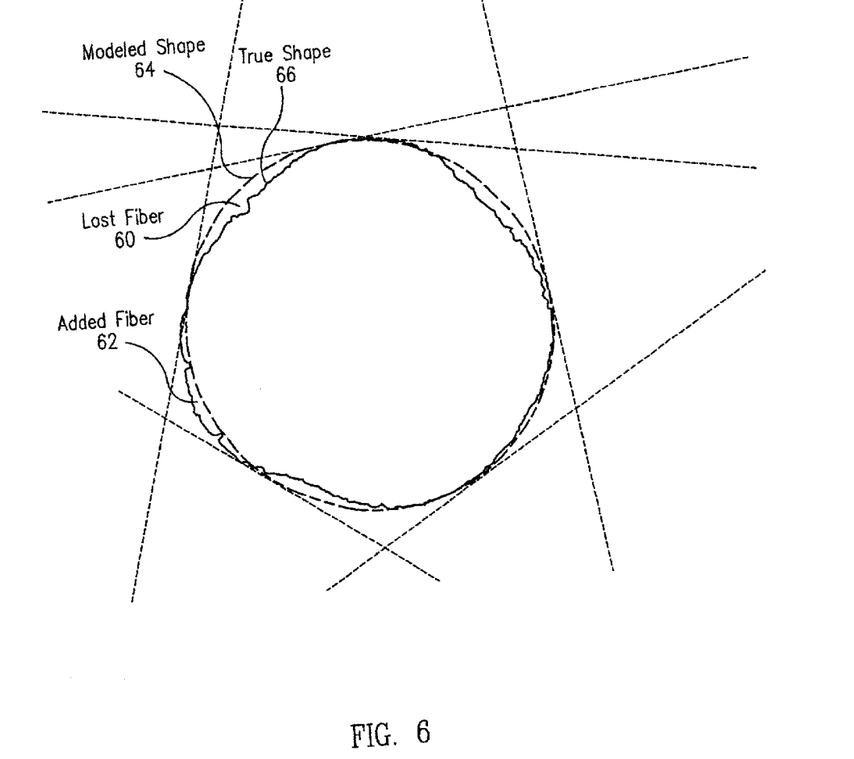
FIG. 6 is a comparison of the modeled shape of the log with the true shape.

For only two sources and two sensors, four tangent lines can be measured and the outer shape can only be modeled as a circle, as there are only three unknowns in this case: the center $x_0$ and $y_0$ and the radius, r. For three sources and three sensors, six tangent lines are measured, and fit to an arbitrarily oriented ellipse that models the log. These six lines can be used to solve the equation for an arbitrarily oriented ellipse, which contains the following unknowns: $x_0$, $y_0$, the location of the center of the ellipse, $\theta$ the angle of rotation of the ellipse, and a, the major axis, and b, the minor axis. Therefore, there are six equations and only five unknowns, so the problem is over-determined. A least squares fit can be made to the data, to find the ellipse most closely fitting the data. The method for determining the best fitting ellipse is set forth in "Determination of cross sectional shape of softwood logs from three x-ray projections using an elliptical model," S. Skatter, Holz als Roh- und Werkstoff 56 (1998) pp. 179–186, which is incorporated herein by reference. An example of such a modeled shape, compared to the true cross sectional shape, is shown in FIG. 6, where the dashed lines 64 represent the modeled shape and the solid lines 66 represent the actual shape. The estimation of the ellipse shape corresponds to step 110 in flow chart of FIG. 3.

The effectiveness of the approximated shape in predicting the attenuation of the actual log can be evaluated in terms of a comparison between the modeled shape and the true shape. Areas in which the modeled shape overestimates the true shape are shown as added fiber regions 60; areas in which the modeled shape underestimates the true shape are shown as lost fiber regions 62. A comparison of the modeled shape to the true shape, for a population of 13 Radiata Pine logs, reveals that the average lost fiber is 1.4%, and the average added fiber is 3.8% with this method. An example of lost and added fiber areas is shown in FIG. 6. The discrepancy is due to shape irregularities of the logs, and the fact that the logs are not perfect ellipses.

The modeled shape and density can be further improved by using an interpolation correction based on the deviation between the expected attenuation based on the modeled shape, compared to the measured attenuation. This correction corresponds to step 120 in the flow chart of FIG. 3. To perform such a correction, two or more points on the ellipse are chosen that are intermediate to the tangent locations. For these points, the expected value of the attenuated signal is estimated from the modeled ellipse, and compared to the actual values measured at these points on the detectors. The model shape is then adjusted to match more closely the measured number by adding a linear correction term to the shape in polar coordinates $r'(\theta)=r(\theta)+$ correction term. The correction term can increase the radius of the modeled shape in the event that a greater attenuation is measured than predicted, or narrow the radius of the modeled shape in the event that less attenuation is measured than predicted. The correction term drops linearly to zero at the tangent points, so that the modeled shape continues to agree with the measured shape at the tangent points. The correction step is shown in the flow chart as the feedback loop 120 in FIG. 3.

A second method for improvement of the modeled shape, is to use the error based on the measured tangent line versus the fitted tangent line, wherein the error arises from having an over-determined system. There are six independent data points, and only 5 unknowns. Therefore after performing the least squares fit of the data to determine the best-fitting ellipse, the radius of the ellipse can be interpolated based on the error remaining at each tangent point.

Another feature of the present invention is to model the internal density boundaries of a solid body, such as the heartwood/sapwood boundary of the log, which in this example is Radiata Pine. The boundary between these regions of different density is readily apparent in FIG. 4, as the second abrupt change 50 in the slope of the attenuated signal across the array of detectors. The heartwood/sapwood boundaries are typically the highest points 50, 52 (maximum attenuation) in the projection, as these rays traverse the longest path of high-density sapwood, before entering the boundary of the lower density heartwood. The heartwood/sapwood boundary is located at the maximum of the signal after the outer shape boundary is detected, as is indicated at points 50 and 52 of FIG. 4. To qualify as a maximum, the location has to be a maximum with respect to its nearest neighbors, and with respect to the neighbors some (e.g. four) pixels away. In order to make the technique more resilient against defects, a filter is applied longitudinally on the list of boundary pixels. The convolution filter used is [1 2 3 2 1]/9.

Having located the boundary pixel, the tangent line to this pixel is calculated knowing the location of the x-ray source, and the boundary point is fitted to an arbitrarily oriented ellipse, in the same manner as was used to model the outer shape. The shape of the heartwood boundary will also define a longitudinal axis, which is the approximate centerline (the pith) of the log. This centerline will provide an origin for the trajectory of knots, which will be explained hereinafter.

Now having the equation of an ellipse closely describing the outer shape of the log, and another ellipse describing the shape of the heartwood boundary, an estimate of the density in each region can be obtained. An arbitrarily oriented ellipse can be created from a unit circle by applying the affine transformations: scaling, translation and rotation. Computing these transforms with the knowledge of the ellipse shape, the inverse transform can be applied to an arbitrary chord traversing the ellipse. Having applied the inverse transform, it is only needed to locate the intersection of the transformed lines with the unit circle. The line intersections are then scaled back to the values they would have traversing the ellipse, so that the path length through the wood is determined in a straightforward manner.

For any given ray path traversing the log, the mass attenuation coefficient, corrected for beam hardening, is readily determined by the value of the attenuated signal at the appropriate detector. The average density $\rho$, along the ray path is obtained by dividing the signal at the detector by the intersection length L, and the mass attenuation coefficient $\mu$. For example, the sapwood density is obtained by choosing a ray path that traverses exclusively sapwood, correcting for the mass attenuation coefficient, and knowing the length of the chord L through the sapwood, the density is readily determined by the value of the attenuated signal. Then choosing a ray which traverses a substantial portion of heartwood, such as a diagonal chord through the center of the ellipse, and subtracting the known attenuation due to the contribution of the sapwood, the remaining density of the heartwood is readily determined. Since many measurements are available for each longitudinal position, the average of these can be computed to give an estimated density.

Assuming these densities are uniformly distributed in the heartwood and sapwood, a modeled view of the log can be generated showing the approximated shape, the heartwood and sapwood boundary, and the densities in each region. An equalized view can be generated by subtracting the modeled view from the projection data, which highlights variations from the normal density, thereby revealing the locations of knots in a given projection. The generation of the equalized view is step 135 in the flow chart of FIG. 3.

The longitudinal locations of the knots or defects can be measured from a longitudinal density map, which is obtained by monitoring the output of each individual detector during the transit of the entire length of the log in front of the detector. The output of each individual detector is therefore a view of a longitudinal slice down the log, and as such is dominated by slowly varying features of the gross geometry of the log, such as its width and curvature. To separate these effects from the higher frequency defects of interest, the output of the detector can be filtered by any of a number of filtering techniques.

Figure 7:
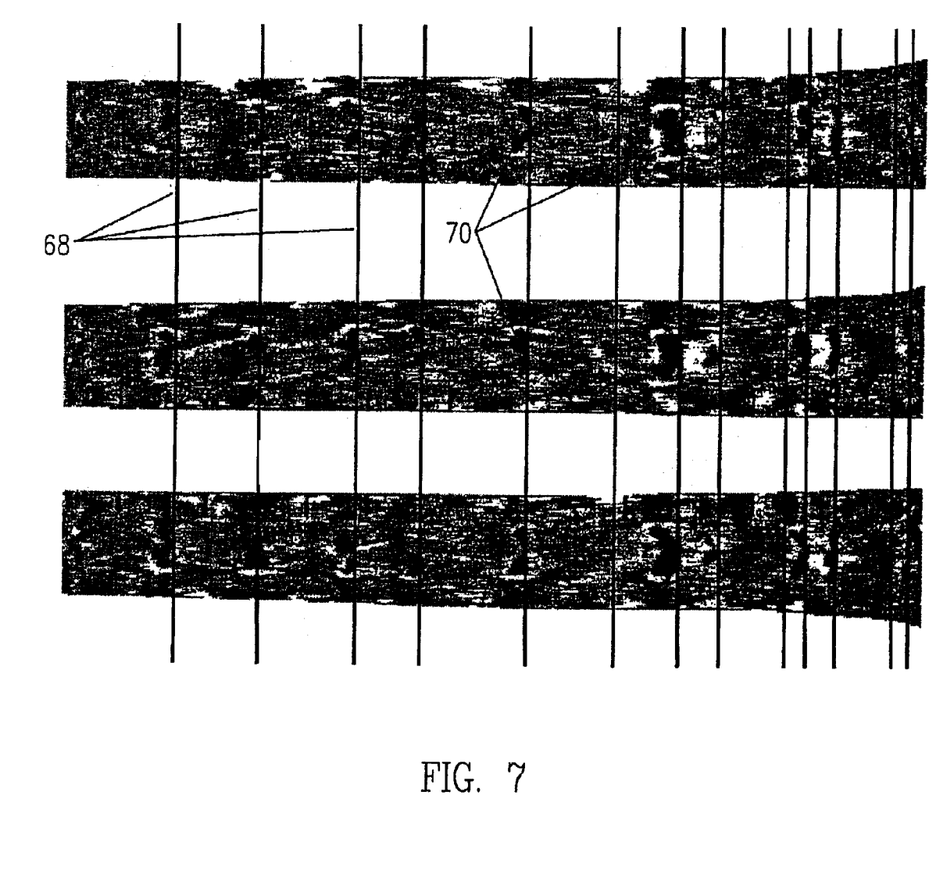
FIG. 7 is a filtered signal showing the longitudinal locations of knots in a log

The first filtering technique is to fit the longitudinal data to a high degree polynomial, wherein a coefficient is assigned to each power of the polynomial in order to fit the curve to the measured data. Upon subtracting this polynomial fit from the data, slowly varying quantities, such as changes in log width or curvature, are filtered out and the remaining signal reflects primarily knots in the wood. The generation of the longitudinal density map corresponds to step 140 of the flow chart of FIG. 3. Exemplary data are shown in FIG. 7, which is a longitudinal density map from which a fifteen-degree polynomial was subtracted. In this example image, the dark colored areas correspond to the knots, labeled 70 in the figure, and the origin or base of each knot whorl is indicated by the vertical lines drawn through the image, indicated as lines 68. This origin is used to compute the trajectory of the knots emanating from each origin, as is explained below.

Another filtering technique is a simple high pass filter, to separate the high frequency signal effects from the lower frequency geometrical effects. Using a series of low pass filters of various kernel lengths, and subtracting the output of the filter from the original signal, yields a map of the high frequency variations. Such a filter however requires knowing the number of pixels comprising a knot boundary, which is in turn related to the rate of relative motion between the log and the scanner and what is selected as a representative knot in the scanning direction. Multiple iterations might be required of a convolution filter over various lengths of the signal, in order to separate the proper frequency range from the lower frequency noise. However the high pass filter has the advantage over the polynomial fit as it is applicable to the data as it is received, rather than waiting for a full row to be received before applying the polynomial fit approach.

The first step in locating the knots is the localization of the longitudinal position of the branch whorls, which are the clusters of knots radiating from the same point in the pith. To make this determination, the high-pass filtered data in all three views is summed together for each pixel that is inside the heartwood boundary. Then the positive peaks are identified as possible knot whorl locations. Within a peak, the point of maximum derivative is taken as the lower edge of the whorl, which gives the point of origin of all the knots in the whorl. This is based on the assumption that the knots are angled upwards. The point of origin is then the pith position as the middle point between the two heartwood boundaries, and the longitudinal position as described here. Determination of the knot whorls is step 150 in the flow chart of FIG. 3.

Having found the longitudinal positions of the candidate features for knots, it remains to estimate the growth trajectory and extent of the knots. This process includes steps 170, 180, 190, and 200 in FIG. 3. This is done by analyzing the data in the near vicinity of the candidate knot, along the z-axis, and material between the candidate locations is not considered. For the first part of this method, pixels within the heartwood core only are considered, as they provide higher contrast to the knot than the surrounding sapwood.

To trace the knot trajectory, a line parameter transformation is performed in a window around the point of origin. The transformation technique is the Hough transform, well known in image processing applications. The window is pre-processed by thresholding, in which each pixel in the window is compared to a threshold value, chosen so that, for example, only a given percentage (e.g. 20%) of the pixels fall above the threshold. In addition, a second threshold value can be chosen, so that for example, only a subset (e.g. 5%) of the pixels is above the value. These two processes are additive, so that each pixel after thresholding has a value of 0, 1 or 2. Then, all of the non-zero pixels are transformed into line parameter space, which plots all the values of line parameters k and b, which define a line $y=kx+b$ that intercepts the pixel. Each point on the line in line parameter space falling on a given cell gives the cell one "vote". Therefore, each non-zero pixel in real space, which generates a line in parameter space traversing a given cell, casts another vote for that cell.

The slope parameter space is divided into a number of different intervals (e.g. 30–40), limited to a maximum and minimum angle, which is based on knowledge of the angles of tree branches found in various species. For Radiata Pine, the maximum angle is taken at 65 degrees. Typically, this parameter needs to be tuned from species to species, however the value of 65 degrees is acceptable for most softwoods. The minimum angle used for Radiata Pine is zero degrees. The slope parameter space is further limited by applying knowledge of the direction of the root end of the log.

The line parameter, or Hough transform generates grid of k and b values, and those points with the largest numbers of votes are the candidate knot trajectories. Ideally, the values of k all correspond to a single value of b, where b is the origin of the knot whorl. If no single point b is clearly preferred, then the several contenders are re-transformed into real space and a least-squares fit is performed on the candidate lines to determine the best central point of origin. If the origin is well chosen, the transform in line parameter space will yield a series of results, all of which fall on a given value of b, and represent knot trajectories with different values of k, all emanating from the same point of origin.

Now that the whorl origin is known, another line parameter space transform is performed. However, now the intercept is fixed and only the slope varies. This means that this transform is much faster, only computing a one-dimensional Hough transform. An improvement in this method uses prior knowledge of the growth trajectories of knots in the species of interest. Literature shows that the square root function, given by the equation $y=k\sqrt{x}$, more closely simulates the trajectories of knot growth than a linear equation. This has been validated for the species Norway spruce and Scots pine, for example in 2000 Oja, J. Evaluation of knot parameters measured automatically in CT-images of Norway spruce (*Picea abies* (L.) Karst). Holz als Roh- und Werkstoff 58 (2000) 5, 375–379, incorporated herein by reference. Values other than the square root can be used. For example, good results for Radiata Pine were achieved with a power of 0.75 (instead of 0.5). The results of this one-dimensional transform are a series of maxima falling on certain values of the slope k, emanating from a single point of origin, b. The maxima correspond to the knot trajectories.

To estimate the lateral extent of the knot, a knot probability along the trajectory is computed, in which the probability is determined by placing a window over the knot trajectory, and computing the average of the pixel values of the high-passed signal bounded by the window. The result is then compared with the median values from a window placed below the knot trajectory, or beyond it. If the value of this difference falls below a certain threshold value, then it is concluded that the knot probability drops to a level at which the trajectory ends. (Practitioners will appreciate that, for our example of Radiata Pine, knots in the lower portion of the tree may not extend into the sapwood due to branch trimming that occurs while the tree is still growing.) For knots projecting into the sapwood, a similar approach is used, except that the probabilities are based on the equalized view in addition to the high-pass filtered data. In general, there is less contrast in detecting a knot whorl in the sapwood because the higher density of the surrounding material more closely matches that of the knot itself.

Figure 8:
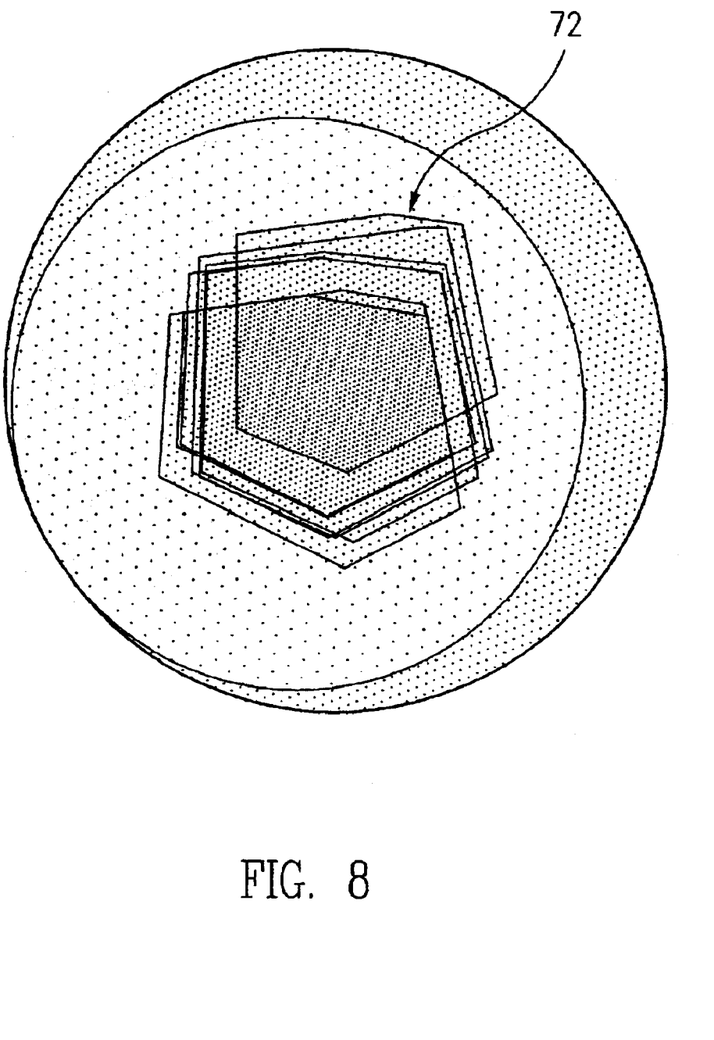
FIG. 8 is a collapsed view of a log showing the knot core.

Finally, the result of the line parameter space transform is a series of knots or defects, whose trajectories in the x-ray projections are known. The trajectories have a longitudinal as well as a transverse dimension. The calculation of the knot trajectory is step 200 in the flow chart of FIG. 3. These results can be summarized by assigning a bounding polygon to each knot whorl, and projecting the polygon along the z-axis. The estimate of the bounding polygon is step 210 of the flow chart of FIG. 3. The bounding polygon is the shape that just encloses the knot whorl. An example of a set of bounding polygons is shown in FIG. 8, wherein the bounding polygons are overlapped in the z-axis, and the gray scale values area added together. The overlapped polygons are indicated by reference numeral 72 in the figure. Finally, the knot core is a bounding box in the collapsed view along the z-axis, whose perimeter encloses each of the knot whorls. A sawing decision, step 230 in flow chart of FIG. 3, can be made based upon the size and dimensions of the knot core. The sawing decision will include a selection of the skew angle, the rotation angle, and the distance from the center of the log along which to make a first cut.

The rotation angle is defined relative to a datum marked on the trunk of the log by pigment, or a saw cut, or other means for providing an indelible mark. The orientation of the log relative to the saw blade is then changed according to the data from the model, by means of an orientation control apparatus. Alternatively, the log need not be marked if it is scanned immediately prior to the sawing, and the relative orientation of the saw blade can be controlled. A third possibility is to rescan the log at the headrig carriage with an external scanner and thus match the rotational position by matching the exterior shape to the x-rayed image. Finally the log is sawed, as the final step 230 in the flow chart of FIG. 3.

A bucking decision can also be made, based on the data obtained from the above described imaging. Bucking relates to the segmentation of the log into intermediate lengths before sawing down the longitudinal axis. The bucking decision can be made before sawing by the software, based on the analysis of the knot core described above, and with input from the operator on the desired lengths of the log segments.

Alternatively, the information generated according to this invention, can be used to grade or sort the logs into bins that correspond to various levels of quality of the log, as in step 240 of FIG. 3. For example, knottiness, bumpiness, or curvature can comprise measurements of quality based on which a sorting decision can be made. The sorting decision can also apply a price decision to the log, based on a previously defined relationship between price and quality.

Another aspect of this invention, which may affect the sorting decision, is the detection of needle flecks. Needle flecks are narrow radial defects common in Radiata Pine, that result from the inclusion of needles into the sapwood of the growing tree, which leave a narrow trail of higher density growth radiating out from the log core. Needle flecks are detected along a narrow window of incident radiation, which traverses the near-center of the log. The measurement window is +/− 15 detector positions about the center of the image. Therefore, a technique within this invention for detecting needle flecks only looks at x-rays, which are nearly parallel to the needle flecks. By looking at high frequency variations in the wood density within this region, the number of needle flecks can be estimated. Then, by assuming a random distribution of these defects, the total number of defects per log is just the number detected multiplied by the ratio of the total volume to the imaged volume of the log. This method has proven effective at grading or distinguishing logs with a high number of these defects from those with a low number. Knowledge of needle flecks generally does not affect the sawing decision, so that this portion of the invention is not shown in the flow chart of FIG. 3. However, the presence of needle flecks may be a part of the sorting decision described above.

In accordance with another embodiment of the present invention, the number of annual rings can also be measured with the apparatus and methods herein. In this embodiment, the total number of rings in a cross section is counted. The ring count is executed in a defect free zone, that is an area along the z-axis that does not contain a knot whorl. A filter is applied along the detectors in the z-direction, which reduces the noise in the image, and a smoothing filter is applied across the detectors. Lastly, a 7-pixel filter is applied across the detectors of magnitude [−1−5 1 10 1−5−1], which enhances peaks and valleys, and creates a signal that oscillates around zero. The rings are then counted by counting local maxima, that is, those pixels, which have a value (i.e. density) higher than their left and right neighbors. The median value of the counts is taken from the projections of each of the (three) views. The number of detected rings calculated by this method, compared to those counted in a true cross section of the log, is low by half a ring, i.e. −0.5 rings, with a standard deviation of 1.4 rings. Since the annual ring count generally does not affect the sawing decision, this portion of the invention was not included in the flow chart of FIG. 3. However as with needle flecks, the annual ring count can be part of the information that determines a sorting decision for a given log.

An appendix attached hereto provides a source code listing for a computer program that may be used to implement the above method.

The embodiments described above are exemplary only and are not intended to be limiting. One skilled in the art may recognize various possible modifications that are intended to be within the spirit and scope of this disclosure. As such, the invention is limited only by the following claims.

APPENDIX B

The following is a list of the files contained on the compact disks.

| File | Date | Size |
|---|---|---|
| analyzeBoundaryMod.m | Jun. 21, 2002 | 8.62 kB |
| attenuationCoeff.m | Jun. 6, 2002 | 415 bytes |
| boundingBox.m | Apr. 18, 200 | 3.18 kB |
| boundingBoxRaster.m | Jul. 12, 2002 | 1.12 kB |
| countNeedleFlecks.m | Jan. 4, 2002 | 1.15 kB |
| countRings.m | Dec. 19, 2001 | 480 bytes |
| CT_Parameters.m | Jun. 19, 2002 | 919 bytes |
| DensityCookies.m | Jan. 14, 2002 | 760 bytes |
| ellipseIntersection.m | Jan. 2, 2002 | 909 bytes |
| ellipses.m | Jul. 8, 2002 | 11.1 kB |
| equalized3View.m | Jul. 12, 2002 | 5.08 kB |
| findShape.m | Aug. 28, 2002 | 5.77 kB |
| findWhorlPos.m | Aug. 28, 2002 | 6.72 kB |
| getLogList.m | Dec. 21, 2001 | 140 bytes |
| isInEllipse.m | Apr. 22, 2002 | 465 bytes |
| KnotsAllLogs.m | Jan. 3, 2002 | 997 bytes |
| KnotAndRings.m | Jan. 10, 2002 | 8.57 kB |
| KnottyCore.m | Jul. 25, 2002 | 26.5 kB |
| NeedleFleck.m | Aug. 28, 2002 | 5.88 kB |
| plotEllipse.m | Apr. 22, 2002 | 683 bytes |
| plotEllipse3D.m | Jun. 5, 2002 | 718 bytes |
| plotLine.m | Dec. 10, 2001 | 1.45 kB |
| readAllShapes.m | Jan. 3. 2002 | 308 bytes |
| readBoundary.m | Dec. 10, 2001 | 1.45 kB |
| readCookies.m | Jan. 10, 2002 | 3.37 kB |
| ReadCT.m | Aug. 28, 2002 | 820 bytes |
| readgain.m | Dec. 21, 2001 | 483 bytes |
| readKnotBoundary.m | Mar. 22, 2002 | 1.89 kB |
| readoffset.m | Dec. 21, 2001 | 275 bytes |
| readRaw3view.m | Jun. 3, 2002 | 2.99 kB |
| ReadSlicePos.m | Dec. 21, 2001 | 628 bytes |
| RingsAllLogs.m | Jan. 4, 2002 | 1.21 kB |
| SetDir.m | Jun. 18, 2002 | 2.27 kB |

APPENDIX B-continued

The following is a list of the files contained on the compact disks.

| | | |
|---|---|---|
| ShapeAllLogs.m | Jun. 21, 2002 | 245 bytes |
| StatsForAllLogs.m | Jun. 21, 2002 | 1.20 kB |
| ThreeViewSampling.m | Jun. 17, 2002 | 1.41 kB |
| trueRings.m | Feb. 21, 2002 | 1.18 kB |
| CTmenu.m | Jun. 20, 2002 | 756 bytes |
| CTPicker.m | Jul. 9, 2002 | 29.8 kB |
| CTPickerBak.m | Jun. 28, 2002 | 23.7 kB |
| PickPointShowTangentInCT.m | Jun. 20, 2002 | 1.31 kB |
| PickProjection.m | Jun. 18, 2002 | 1.67 kB |
| pickProjectionFromCT.m | Jul. 18, 2002 | 4.47 kB |
| plotCTLine.m | Jun. 19, 2002 | 0.98 kB |
| projectionMenu.m | Jun. 19, 2002 | 335 bytes |
| threeviewmenu.m | Jul. 2, 2002 | 94 bytes |
| filelist.txt | Aug. 28, 2002 | 1.58 kB |

What is claimed is:

1. An apparatus for measuring internal structures of a body, the apparatus comprising:
   two or more sources of electromagnetic radiation, with some of said sources separated from a first said source by less than 120 degrees of arc, and two or more arrays of detectors, each of said arrays paired with a corresponding source and disposed apposite from the corresponding source, the detectors of each array being arranged adjacent one to another and each capable of outputting a signal indicative of the level of radiation received from the corresponding source, wherein the corresponding sources and arrays are disposed so that the body is passed between them in a manner that attenuates the radiation received by the arrays; and
   a computer programmed to measure a difference in the output signal of adjacent detectors, thereby estimating a line between sources and detectors, which is tangent to a boundary of the internal structures of the body, and modeling from the estimated tangent line an approximate shape of the boundary of the internal structures.

2. The apparatus in claim 1, wherein there are three of said sources of electromagnetic radiation.

3. The apparatus of claim 2, wherein two sources are separated from a first source by less than 90 degrees of arc.

4. The apparatus of claim 3, wherein the body is a log.

5. The apparatus of claim 4, wherein the approximate shape of the boundary of the internal structure is modeled to be an arbitrarily oriented ellipse.

6. The apparatus of claim 5, wherein each of the pairs of detector arrays and corresponding sources is disposed in a different plane, transverse to a longitudinal axis of the log.

7. The apparatus of claim 5, wherein the measured difference in output signal are a result of a boundary between the internal structures, which are heartwood and sapwood in the log.

8. The apparatus of claim 5, wherein the measured difference in output signal are a result of a boundary between the internal structures, which are bark and sapwood in the log.

9. The apparatus of claim 5, wherein the computer is further programmed to calculate a second derivative of said output signal between adjacent detectors.

10. The apparatus of claim 9, wherein the second derivative indicates a boundary between internal structures, which are bark and sapwood in the log.

11. The apparatus of claim 6, further comprising a means for transporting the log past the sources and the detectors, in a direction parallel to the longitudinal axis of the log.

12. The apparatus of claim 11, wherein the computer is further programmed to store the output signal of the detectors as a function of time as the log passes by the sources and detectors, thereby generating a density map of the log along the longitudinal axis.

13. The apparatus of claim 12, wherein the computer is further programmed to apply a high pass filter to the density map, thereby generating a map of longitudinal high frequency variations in the density map of the log, wherein the high frequency variations correspond to knots in the log.

14. The apparatus of claim 13, wherein applying the high pass filter comprises applying a series of low pass filters of varying kernel length, and subtracting the filter output from the density map.

15. The apparatus of claim 13, wherein applying the high pass filter comprises subtracting a polynomial fit of high degree from the density map.

16. The apparatus of claim 13, wherein the computer is further programmed to determine an orientation of the log for presentation to a sawmill blade, based on the map of high frequency variations corresponding to knots in the log.

17. The apparatus of claim 16, further comprising a means for rotating the log into the orientation, for presentation to the sawmill blade.

18. A method for measuring internal structures of a log, said method comprising:
   providing two or more sources of electromagnetic radiation disposed around a perimeter of the log, with some sources being separated from a first source by less than 120 degrees of arc, and two or more arrays of adjacent detectors, each of said arrays being paired with a corresponding source, and disposed about the log on an opposite side from the corresponding source, with each detector outputting a signal indicative of a signal intensity emitted from the source and attenuated by the log;
   measuring the output signal of each of the arrays of detectors;
   calculating, based on the measured output signal of each of the arrays of detectors, a line between the sources and the detectors, which is tangent to a boundary of the internal structures, and modeling from the calculated tangent lines an approximate shape of the boundary of the internal structures; and
   modeling the approximate shape of the boundary of the internal structures as an arbitrarily oriented ellipse.

19. The method of claim 18, wherein some of said sources are separated from a first source by less than 90 degrees of arc.

20. The method of claim 18, wherein each pair of detector with its corresponding source is located in a different plane, transverse to a longitudinal axis of the log.

21. The method of claim 20, wherein the signal output from each detector is measured sequentially, as the log passes each plane containing the pair of the source and the detector.

22. The method of claim 18, further comprising correcting the approximate shape of the arbitrarily oriented ellipse, based on a difference between a measured output signal and an expected output signal, based on the approximate shape.

23. The method of claim 18, further comprising correcting the approximate shape of the arbitrarily oriented ellipse, based on a difference between a measured tangent point and a modeled tangent point, based on the approximate shape.

24. The method of claim 18, further comprising calculating a second derivative of the output signal between adjacent elements in the array.

25. The method of claim 24, wherein the second derivative indicates a boundary between the internal structures, which are bark and sapwood in the log.

26. The method of claim 18, wherein the tangent line is a tangent to a boundary between internal structures, which are heartwood and sapwood of the log.

27. The method of claim 18, wherein the tangent line is a tangent to a boundary between internal structures, which are bark and sapwood of the log.

28. The method of claim 18, further comprising storing the output signal of the detectors as the log is transported past the sources and detectors, in order to generate a density map of the log in a direction parallel to a direction of motion of the log passing the sources and detectors.

29. The method of claim 28, further comprising applying a high pass filter to the density map in order to generate a high pass filtered image which highlights longitudinal positions of knots in the density map of the log.

30. The method of claim 29, wherein applying the high-pass filter comprises subtracting a polynomial fit of high degree from the density map.

31. The method of claim 29, wherein applying the high-pass filter comprises applying a series of low pass filters of varying kernel length to generate a filter output, and subtracting the filter output from the density map.

32. The method of claim 29, further comprising determining knot whorl longitudinal positions by summing the high pass filtered images generated by each source and detector, and determining a point of maximum slope as corresponding to a longitudinal position of a knot whorl.

33. The method of claim 32, further comprising determining a knot trajectory by performing a line parameter Hough transform around the longitudinal positions of the knot whorl, using a middle point between heartwood boundaries as an origin for a line parameter space.

34. The method of claim 33, further comprising re-transforming maxima in the Hough transform back into real space, and performing a least-squares fit to determine an estimate for a point of origin of a knot whorl.

35. The method of claim 33, further comprising performing another Hough transform, using a fixed intercept, and varying only a slope of a line in Hough space.

36. The method of claim 33, further comprising performing a Hough transform wherein a slope of the knot trajectory is non-linear, such that y depends on x raised to a power between zero and one.

37. The method of claim 33, further comprising using an expected angle of knots in a species of the log and a direction of a root end of the log, to limit a number of possible slopes of lines in line parameter space.

38. The method of claim 33, further comprising computing a knot probability to determine an extent of the knot trajectory.

39. The method of claim 38, further comprising grading the log in terms of location and extent of the knot trajectories.

40. The method of claim 38, further comprising estimating a bounding box for a knotty core of the log, based on the extents of knot trajectories.

41. The method of claim 40, further comprising grading the log in terms of the bounding box for the knotty core, based on the extents of the knot trajectories.

42. The method of claim 40, further comprising determining a rotation angle of the log relative to a saw blade, based on the estimate of the bounding box for the knotty core.

43. The method of claim 42, further comprising rotating the log to the rotation angle.

44. The method of claim 18, further comprising counting a number of needle flecks radiating from a core of the log, based on a number of high frequency variations occurring in a window of less than about 5 degrees from a center of a detector array.

45. The method of claim 44, further comprising grading the log based on the number of needle flecks counted.

46. The method of claim 18, further comprising counting a number of annual rings from the output signal.

47. The method of claim 46, further comprising convolving the output signal with a filter and counting the number of local maxima.

48. The method of claim 46, further comprising grading the log based on the number of annual rings counted.

49. A method for measuring thickness of bark on a log, said method comprising:
providing one or more sources of electromagnetic radiation disposed around a perimeter of the log, and one or more arrays of adjacent detectors, which are disposed about the log on an opposite side from the sources, the detectors outputting a signal indicative of a signal intensity emitted from the sources, and attenuated by the log;
providing an external scanning means for measuring an external profile of the log;
measuring an output signal of the array of adjacent detectors;
calculating, based on the measured output signal of the array of detectors, a line between the sources and the detectors, which is tangent to a boundary between bark and sapwood of the log, and between bark and air.

50. The method of claim 49, further comprising calculating a second derivative of the output signal between adjacent detectors in the array.

51. The method of claim 50, wherein the second derivative indicates a boundary between bark and sapwood in the log.

52. The method of claim 51, further comprising measuring a thickness of bark on a log, from the calculated tangent lines to the boundary between bark and sapwood of the log, and the calculated tangent line to the boundary between bark and air.

53. The method of claim 52, further comprising sorting the log according to the measured thickness of the bark on the log.

54. The method of claim 52, wherein the measured bark thickness is subtracted from the external profile as measured by the external scanning means, to establish a shape under bark.

55. The method of claim 54, further comprising sorting the log according to the measured shape under bark.

* * * * *